United States Patent [19]

Chang et al.

[11] Patent Number: 4,480,143

[45] Date of Patent: Oct. 30, 1984

[54] HYDROCARBON SYNTHESIS

[75] Inventors: Clarence D. Chang, Princeton; William H. Lang, Pennington, both of N.J.

[73] Assignee: Mobil Oil Corporation, New York, N.Y.

[21] Appl. No.: 229,610

[22] Filed: Jan. 28, 1981

[51] Int. Cl.³ ............................ C07C 1/20; C07C 1/00
[52] U.S. Cl. ...................................... 585/469; 585/733
[58] Field of Search ............................... 585/469, 733

[56] References Cited

U.S. PATENT DOCUMENTS 2,041,840  5/1936  Lazier et al. ...................... 585/733
4,265,735  5/1981  Audeh et al. ..................... 585/733

Primary Examiner—Delbert E. Gantz
Assistant Examiner—Helane E. Maull
Attorney, Agent, or Firm—Alexander J. McKillop; Michael G. Gilman; Howard M. Flournoy

[57] ABSTRACT

A process for converting or synthesizing hydrocarbons from carbon sulfides such as $CS_2$ by catalytic hydrogenation over catalysts such ZSM-5 type zeolites.

4 Claims, No Drawings

HYDROCARBON SYNTHESIS

BACKGROUND OF THE INVENTION

1. Field of the Invention

This invention is directed to a novel process for converting carbon sulfides with hydrogen to hydrocarbons, particularly aromatics, over ZSM-5 type zeolites which may also contain a metal component having hydrogenation and/or hydrodesulfurization activity. This process is also directed to a means of providing a new inexpensive route directly from carbon sources to synthetic fuels.

2. Description of the Prior Art

Various means have been tried to produce hydrocarbons in a facile, efficient and inexpensive manner. For example, $CS_2$ has been reacted with hydrogen to yield $H_2S$ and a variety of organic compounds dependent upon temperature, pressure, catalyst and reaction medium. At higher temperatures, lower hydrocarbons such as $CH_4$ are produced and at lower temperatures reduction of carbon disulfide produces various organic sulfur compounds such as $CH_3SH$.

U.S. Pat. No. 4,175,928, for example, relates to a process for converting organic sulfur compounds into $H_2S$; a sulfided catalyst having incorporated therein two metal components such as nickel and molybdenum is used in the process.

U.S. Pat. No. 3,894,107 relates to the discovery that hetero organic compounds of the R-X type may be converted to aromatic hydrocarbons by contacting such compounds with a crystalline aluminosilicate zeolite. R stands for an aliphatic hydrocarbon moiety and X stands for a heteroatom such as sulfur, nitrogen, halogen or oxygen.

U.S. Pat. No. 3,894,103 discloses a process wherein lower aliphatic alcohols, carbonyls, ethers, or analogues thereof are converted to higher hydrocarbons by contacting such with a crystalline aluminosilicate zeolite having a silica to alumina ratio of about 60 to 600 to increase the liquid $C_5^+$ yield.

SUMMARY OF THE INVENTION

It has now been discovered that carbon sulfides such as $CS_2$ or COS when reacted with $H_2$ over ZSM-5 type zeolites produce highly useful hydrocarbons, especially aromatics. The zeolite may or may not contain a metal component having hydrogenation and/or hydrodesulfurization activity. Since sulfides such as $CS_2$ are readily produced by the reaction of S with C, $CH_4$ or LPG, the herein embodied process is believed to provide a new, novel method for synfuels production.

DESCRIPTION OF THE PREFERRED EMBODIMENTS

The zeolites useful herein as mentioned previously are of the ZSM-5 type and include ZSM-5, ZSM-11, ZSM-12, ZSM-35, ZSM-38, TEA mordenite and other similar materials and also their hydrogen counterparts such as HZSM-5, etc. They may also be base exchanged, contain ammonium ions or impregnated to contain a cation complement. Examples of useful metal components include Co, Co/Mo, Zn, Zn/Pd, Ni, NiW, and Ni/Mo. Generally speaking, any metal from Groups II or VIII of the Periodic Table may be useful. U.S. Pat. No. 3,702,886 describes and claims ZSM-5; U.S. Pat. No. 3,709,979 describes ZSM-11; ZSM-12 is described by W. German Offenlegungschrifft No. 2,213,109; U.S. Pat. No. 4,016,245 particularly describes ZSM-35 and ZSM-38 is particularly described in U.S. Pat. No. 4,046,859 all of which are incorporated herein in their entirety.

To illustrate the practice of this invention, two ZSM-5 type catalysts were each used to carry out separate reactions wherein $CS_2$ was converted to hydrocarbons. The reaction conditions and products set forth in the Table below are exemplary only and are not meant to limit the invention. The temperature and pressure can vary within wide limits. Preferred is a range of 400° to 1200° F. and a pressure within the range of 100 to 1000 psig. The feed rates used in the reactive process can vary from 0.5 LHSV (liquid hourly space velocity) to about 50 LHSV for $CS_2$ or COS, and 200 to about 10,000 GHSV (gas hourly space velocity) for $H_2$.

The specific embodiments and details as mentioned hereinabove and disclosed below are for the sole purpose of illustrating the invention. It is therefore apparent to those of ordinary skill in the art that various changes and modifications may be made without departing from the scope of the invention.

The feasibility of the novel method embodied herein and the wide range of hydrocarbons obtained, especially aromatics, are demonstrated by the data shown in the Table below:

TABLE

|  | EXAMPLE 1 | EXAMPLE 2 |
|---|---|---|
| Reaction Conditions |  |  |
| $CS_2$, LHSV | 1 | 1 |
| $H_2$, GHSV | 400 | 400 |
| T, °F. | 900 | 900 |
| P, psig | 250 | 250 |
| Catalyst | *HZSM-5 | 50% HZSM-5/$Al_2O_3$ |
|  |  | 50% Co/$SiO_2$** |
| $CS_2$ Conversion, % | 25.6 | 40.3 |
| HC, wt. % |  |  |
| $C_1$ | 52.4 | 44.7 |
| $C_2$ | 9.2 | 6.1 |
| $C_2^=$ | 1.9 | — |
| $C_3$ | 3.0 | 3.7 |
| $C_3^=$ | 0.3 | 0.1 |
| i $C_4$ | 0.2 | 0.2 |
| n $C_4$ | 0.2 | 0.3 |
| $C_4^=$ | — | — |
| $C_5^+$ nonaro | — | tr |
| $A_6$ | 1.4 | 2.6 |
| $A_7$ | 5.9 | 7.7 |
| $A_8$ | 8.2 | 9.5 |
| $A_9$ | 4.6 | 18.1 |
| $A_{10}$ | 0.3 | 3.2 |
| $A_{11}^+$ | 12.4 | 3.8 |

*prepared in accordance with U.S. Pat. No. 3,702,886
**obtained commercially

The unexpected and surprising efficiency of this process, particularly with respect to providing aromatics is clearly shown in the Table. For example, the HZSM-5 catalysts of the present invention, see Example 1, are about as effective as a cobalt containing catalyst, see Example 2, with respect to aromatics. This is most surprising and quite unexpected in view of the fact that HZSM-5 (Example 1) catalyst had a conversion rate for $CS_2$ of only 25.6% compared to 40.3% for the cobalt containing catalyst of Example 2. Even more surprising is the finding that ZSM-5 type materials catalyze the following reaction: $CS_2 + 3H_2 \rightarrow [CH_2] + 2H_2S$ in the absence of a metal hydrogenation component.

We claim:

1. A process for converting as a reactant carbon sulfides selected from the group consisting of $CS_2$ and COS to a hydrocarbon or mixture of hydrocarbons ranging from $C_1$ to $C_{11}+$ wherein at least 25% thereof are $C_5$ to $C_{11}$ comprising contacting said carbon sulfides with a ZSM-5 type aluminosilicate zeolite catalyst having a constraint index of about 1 to 12 and having a silica to alumina ratio of at least 12 at about 400° to 1200° F. and a pressure of about 100 to 1000 psig in the presence of added hydrogen to produce a highly aromatic product.

2. The process of claim 1 wherein the catalyst is selected from the group consisting of ZSM-5, ZSM-11, ZSM-12, ZSM-35, ZSM-38 and their hydrogen forms.

3. The process of claim 2 wherein said catalyst is further comprised of a Group II or Group VIII metal from the Periodic Table.

4. The process of claim 3 wherein the metals are selected from the group consisting of Co, Co/Mn, Zn, ZnPd, Ni, NiW and Ni/Mo.

* * * * *

UNITED STATES PATENT AND TRADEMARK OFFICE
CERTIFICATE OF CORRECTION

PATENT NO. : 4,480,143
DATED : October 30, 1984
INVENTOR(S) : CLARENCE D. CHANG AND WILLIAM H. LANG It is certified that error appears in the above–identified patent and that said Letters Patent are hereby corrected as shown below:

In column 3, line 6, "$C_{11}$" should be --$C_{11}^+$--.

Signed and Sealed this

Twenty-sixth Day of March 1985

[SEAL]

*Attest:*

DONALD J. QUIGG

*Attesting Officer*   *Acting Commissioner of Patents and Trademarks*